US 6,679,279 B1
United States Patent
Liu et al.
Patent No.: US 6,679,279 B1
Date of Patent: Jan. 20, 2004

(54) FLUIDIC VALVE HAVING A BI-PHASE VALVE ELEMENT

(75) Inventors: Robin Hui Liu, Chandler, AZ (US); Justin J. Bonanno, Gilbert, AZ (US); Piotr Grodzinski, Chandler, AZ (US); Randall Stevens, Phoenix, AZ (US)

(73) Assignee: Motorola, Inc., Schaumburg, IL (US)

( * ) Notice: Subject to any disclaimer, the term of this patent is extended or adjusted under 35 U.S.C. 154(b) by 0 days.

(21) Appl. No.: 10/192,297

(22) Filed: Jul. 10, 2002

(51) Int. Cl.$^7$ ................................................. F15C 1/04
(52) U.S. Cl. ........................ 137/13; 137/806; 137/807; 137/828; 137/833; 137/565.37
(58) Field of Search ................................ 137/807, 828, 137/833, 842, 806, 565.37

(56) References Cited

U.S. PATENT DOCUMENTS 5,988,197 A * 11/1999 Colin et al. .................... 137/13
6,536,476 B2 * 3/2003 Ueno et al. .................. 137/828
6,578,596 B1 * 6/2003 Batchelder et al. ...... 137/15.09

OTHER PUBLICATIONS

Kovacs, G.T.A. *Micromachined transducers sourcebook.* 1998. Boston: WCB McGraw–Hill. pp. 823–838.
Henning, A.K., et al. *A thermopneumatically actuated microvalve for liquid expansion and proportional control.* Transducers '97: International Solid State Sensors and Actuators Conference. 1997. pp. 825–828.
Jerman, H. *Electrically–Activated Normally–closed Diaphragm Valves.* Transducers '91. 1991. San Francisco, CA., pp. 1045–1048.
Barth, P.W. *Silicon Microvalves for Gas Flow Control.* Tranducers '95, 1995, Stockholm, Sweden. pp. 276–279.
Krulevitch, P., et al. *Thin film shape memory alloy microactuators.* Journal of Microelectromechanical Systems, 1996. 5(4): pp. 270–282.
Huff, M.A. and M.A. Schmidt. *Fabrication, Packaging and Testing of a Wafer–bonded Microvalve.* IEEE Solid–State Sensors and Actuator Workshop. 1992, pp. 194–197.
Trimmer, W. and R. Jebens. *An Operational Harmonic Electrostatic Motor.* IEEE Workshop on Micro Electro Mechanical Systems. 1989. Salt Lake, Utah. pp. 13–16.
Rogge, B., et al *Fully Batch Fabricated Magnetic Microactuators Using a Tow Layer LIGA Process.* Tranducers' 95, 1995, pp. 320–323.
Meckes, J., J. Behrens, and W., Benecke. *Electromagnetically Driven Microvalve Fabricated in Silicon.* Transducers' 97. 1997, pp. 821–824.
Beebe, D.J., et al.*Functional Structures For Autonomous Flow Control Inside Microfluidic Channels.* Nature, 2000. 404: pp. 588–590.

(List continued on next page.)

Primary Examiner—A. Michael Chambers (57) ABSTRACT

A fluidic valve (125, 300, 500, 900, 1000, 1100, 1200, 1300) switches a state of flow of a fluid in a fluid communication channel of a fluid guiding structure (505). Heating a bi-phase valve element (515, 1065, 1215) causes a change a state of the bi-phase valve element from a high viscosity state to a low viscosity state. A bi-phase valve element that clogs the fluid communication channel can be pushed into an expanded portion (135, 320, 520, 915, 1220) of the fluid communication channel by an application of pressure to the fluid while the bi-phase valve element is in the low viscosity state, unclogging the fluid communication channel. A bi-phase valve element can be pushed from a valve element source chamber (550, 1250) into the fluid communication channel by using a pumped fluid entering the source chamber at a pump inlet (551) while the bi-phase valve element is in the low viscosity state, clogging the fluid communication channel.

32 Claims, 4 Drawing Sheets

OTHER PUBLICATIONS

Quake, S.R. and A. Scherer. *From Micro– to Nanofabrication with Soft Materials.* Science, 2000, 290: pp. 1536–1540.

Anderson, R.C., et al. *Microfluidic Biochemical Analysis System.* Transducers '97. 1997. Chicago, IL., pp. 477–480.

Madou, M. *Fundamentals of Microfabrication.* 1997, Boca Raton, FL: CRC Press LLC: pp. 484–487, 498–501.

Shoji, S. and M. Esashi *Microflow devices and systems.* IOP Publishing Ltd., 1994: pp. 157–171.

Gravesen, P., J. Branebjerg, and O.S. Jensen. *Microfluidics–a review.* J. Micromech. Microeng., 1993. 3: pp. 168–182.

Kaartinen, N. *Micro Electro Thermo Fluidic (METF) Liquid Microprocessor.* Proceedings of the 9th Annual Workshop of Micro Electro Mechanical Systems (MEMS '96), San Diego, CA, Feb. 11–15, 1996, pp. 395–399.

* cited by examiner

FLUIDIC VALVE HAVING A BI-PHASE VALVE ELEMENT

FIELD OF THE INVENTION

This invention relates generally to mechanical valves, and in particular to fluidic valves used for microfluidic applications such as biological assaying.

BACKGROUND OF THE INVENTION

There is a growing demand for biological fluid processing systems that has generated a need for small fluidic valves. One class of biological fluid processing systems consists of disposable systems that are for single use. Many small fluidic valves are under investigation and a few have been distributed commercially. Most of these existing small fluidic valves couple a flexible diaphragm to a thermopneumatic, piezoelectric, electrostatic, electromagnetic, bimetallic, or other type of actuator. They generally suffer from complicated design and are generally too expensive to build. Fabrication of many existing small fluidic valves involves bulk processes (e.g., bulk etching of silicon) and surface processes (e.g., thin film process). Disparate materials (e.g., thin film resistive heaters in thermopneumatic valves, piezo material in piezoelectric valves, TiNi alloy in shape memory alloy valves, etc.) are often used in addition to a substrate material (e.g., Si). Not only is the fabrication process of such small fluidic valves complicated, but the integration into complex, microfluidic devices has also proven to be non-trivial. These types of small fluidic valves have generally found to be undesirable for used in single-use bio-microfluidic devices.

What is needed is a very low cost, highly reliable, microfluidic valve for disposable, single use bio-microfluidic devices.

BRIEF DESCRIPTION OF THE DRAWINGS

The present invention is illustrated by way of example and not limitation in the accompanying figures, in which like references indicate similar elements, and in which.

DETAILED DESCRIPTION OF THE DRAWINGS

A fully integrated, micro-biological analytical device needs to perform all analytical functions including sample preparation, mixing steps, chemical reactions, and detection in an integrated bio-microfluidic device. Most of the currently demonstrated microfluidic or microarray device components pursue single functionality other than sample preparation, and use purified DNA as an input sample. Existing microfluidic and microarray technologies work very well for highly predictable and homogeneous samples common in genetic testing and drug discovery processes. One of the biggest challenges for current biochips, however, is to perform analysis in samples as complex and heterogeneous as whole blood or contaminated environmental fluids. For most biochips (including lab chips and microarray chips), sample preparation is still performed off-chip. Embodiments of the present invention are suitable for the sample preparation function on the micro-fluidic level.

Figure 1:
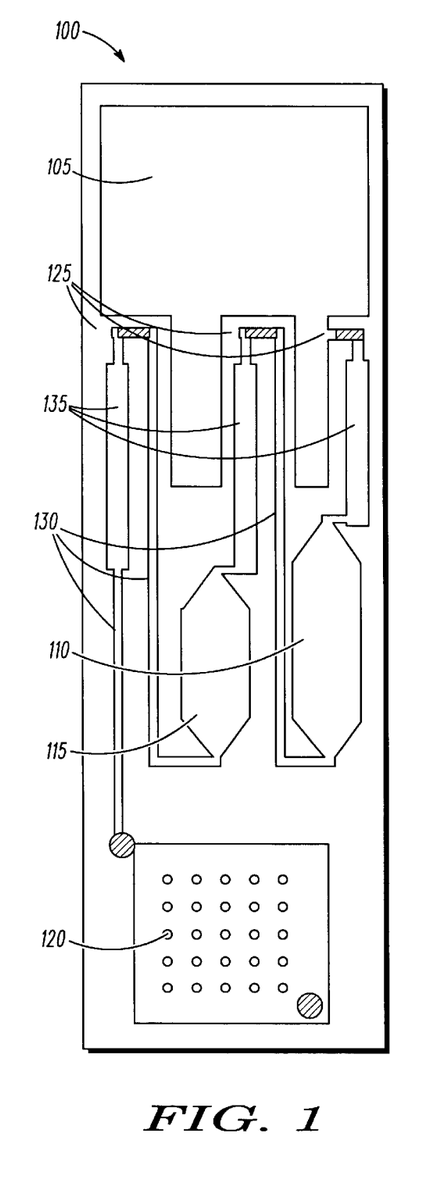
FIGS. 1 and 2 are schematic representations of a fluidic cartridge and a printed circuit board (PCB) that make up a bio-microfluidic device, in accordance with an embodiment of the present invention.
Figure 2:
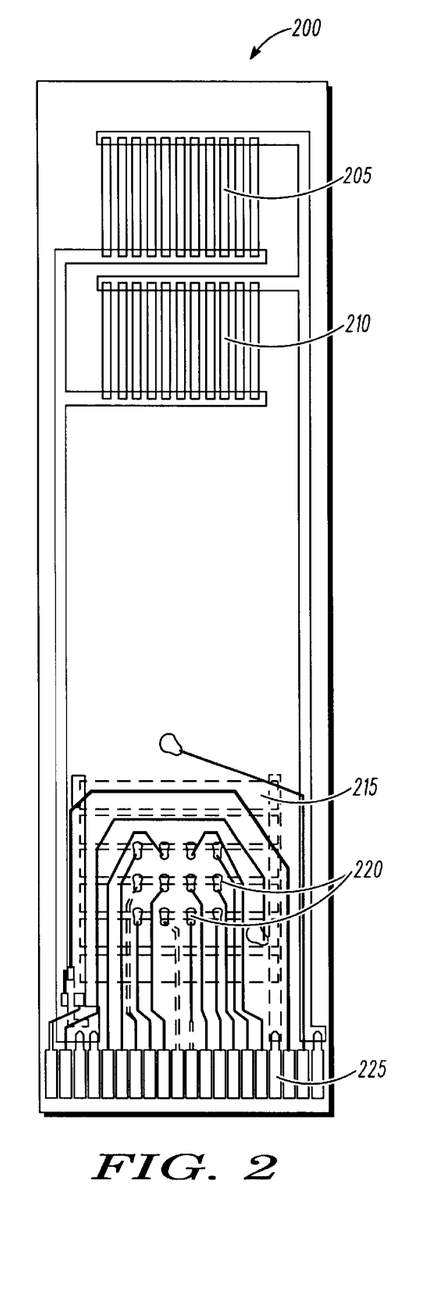

A fully integrated bio-microfluidic device that can both amplify and electronically detect high abundance DNA (deoxyribonucleic acid) targets (e.g., human genomic DNA from diluted blood solution or other bodily fluids) and perform SNP (single nucleotide polymorphisms) detection assays can benefit greatly from embodiments of the present invention. In an example of an integrated bio-microfluidic device, a sample preparation bio-microfluidic module (comprising cell lysis followed by asymmetric PCR (polymerase chain reaction) amplification and mixing with hybridization reagents) made in accordance one or more embodiments of the present invention could be integrated with an electrochemical detection technology to provide a solution leading to a complete sample-to-answer on-chip bio-assay. Referring to FIGS. 1 and 2, schematic representations are shown of a fluidic cartridge 100 (FIG. 1) and a printed circuit board (PCB) 200 (FIG. 2) that make up a bio-microfluidic device when the fluidic cartridge 100 and PCB 200 are bonded together, in accordance with an embodiment of the present invention. The fluidic cartridge 100 is a structure that comprises a self-contained air pump chamber 105, a hybridization buffer storage chamber 110, a polymerized chain reaction (PCR) chamber 115, and a hybridization detection chamber and mixing unit 120, all coupled by fluid communication channels 130, and three paraffin bi-phase valve elements 125. The fluid communication channels 130 have sink chambers 135, the purpose of which is explained below. The PCB 200 contains a pump heater 205, a valve element heater 210, temperature sensors (not shown), a DNA heater 215, detection electrodes (16 are shown) with DNA capture probes (detection electrodes) 220, required circuits (not shown), and contacts for electronic connection 225. The fluidic cartridge 100 is bonded with the PCB 200 in such a way that the pump heater 205 is in contact with the air pump chamber 105 in the fluidic cartridge 100 and the detection electrodes 220 sense a solution when it is in the detection chamber 120 within the fluidic cartridge. The pump heater 205, the valve element heater 210, and the DNA heater (detection chamber heater) 215 are in this example resistive patterns printed on the PCB 200. The bio-microfluidic device in this example is approximately 2.5 centimeters by 8.5 centimeters. The fluidic cartridge in this example is chambered piece of plastic that forms a sealed fluid guiding structure when it is bonded to the PCB 200. In an alternative embodiment, a sealed fluid guiding structure is formed by sealing the fluidic cartridge 100, which is a chambered piece of plastic, with a thin plastic back wall bonded to it. In the alternative embodiment, the DNA capture probes pass through the back wall and are sealed to it.

In this example, a sample input to the PCR chamber 115 is a 60 uL mixture that contains a 2 microliter sample of blood or a purified DNA sample as well as PCR reagents that amplify the sample in a PCR product. The hybridization buffer storage chamber 110 is loaded with 60 uL hybridization buffer and reagents, which will mix with the PCR product in the PCR chamber 115 following the PCR amplification and will be subsequently pumped into the detection chamber 120 for hybridization assay. The material structure of the fluidic cartridge 100 is compatible with PCR amplification and is capable of a low level of multiplexing in the single PCR chamber 115. The detection chamber 120 in this example has 16 detection electrodes. The bio-microfluidic device of this example is for use in conjunction with an instrument that provides required power supply and ambient heating/cooling capabilities needed for amplification thermal cycling, temperature monitoring, and data acquisition.

After a user loads a sample and reagents via pipetting into the PCR chamber 115 and the hybridization buffer storage chamber 110, the device is plugged into the instrument, in a vertical orientation. An asymmetric PCR can then be performed in the PCR chamber 115 using a heating block incorporated within the instrument. After the PCR reaction is completed, the pump heater 205 in the PCB, can be activated. As a result of the localized heating of the pump chamber 105, air in the pump chamber will expand and act as a forward pump. At the same time, the valve element heater 210 will melt the three bi-phase valve elements 125, which are composed of paraffin, (needed there to initially isolate the PCR chamber 115 from the hybridization buffer storage chamber 110 during the amplification reaction). The pressure from the heated air in the air pump chamber 105 will cause the melted paraffin bi-phase valve elements 125 to flow into the sink chambers 135, which are expanded portions of the fluid communication channels 130, where the paraffin resolidifies along the walls of the sink chambers 135 of the fluid communication channels 130, thereby opening the fluid communication channels 130 connecting the chambers. The pressurized air from the air pump chamber 105 can then move the hybridization buffer into the PCR chamber 115, mixing with the PCR product, and then move the mixed solution into the detection chamber 120 for hybridization. During the hybridization, the DNA heater 215 in the PCB 200 will maintain the temperature of the reaction solution at a required level. An acoustic mixing can be implemented in the detection chamber 120 to enhance mixing between the solutions, and also between the target DNA in the solution and the detection probes 220 on the electrodes. The instrument can scan the detection electrodes at required intervals until the hybridization is completed (signal saturation). The bio-microfluidic device requires no user intervention between the initial loading of sample and reagents and final assay completion, other than loading the device into the instrument and initiating the instrument's operation. The assay should be completed in less than 4 hours.

Since the bio-microfluidic device is operated vertically and the amount of fluid is on the order of tens of microliters, fluid gravity is considered together with other forces such as liquid/gas interface force and surface tension in the design of the fluidic cartridge 100. For example, the surface-to-volume ratio of the cartridge is implemented high enough so that the air/liquid surface tension is able to hold air bubbles in place, without the bubbles moving upward and causing unexpected effects.

The PCR chamber 115 is thermally isolated from the air pump chamber 105 and the paraffin bi-phase valve elements 125 by, for example the choice of plastic and the relative locations of the functions, so that during the PCR reaction when the PCR chamber 115 is thermally cycled for 1–2 hours, the air pump chamber 105 and the paraffin valve elements 125 remain at relatively low temperature. The pump, valve element, and detection chamber heaters 205, 210, 215 in the bio-microfluidic device are implemented to be in good contact with the fluidic cartridge 100 to ensure an efficient thermal transfer. Temperature sensors are used to detect and regulate the temperature in the PCR chamber 115 and detection chamber 120.

The above description of a bio-microfluidic device is just one example of a fluidic device that can benefit from one or more embodiments of the present invention. Other embodiments are described below that can be used in a wide variety of fluidic devices.

Figure 3:
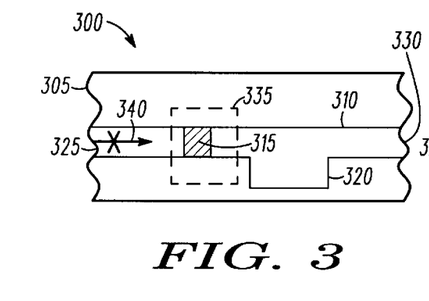
FIGS. 3 and 4 are schematic representations of a close-open fluidic valve, in accordance with an embodiment of the present invention.
Figure 4:
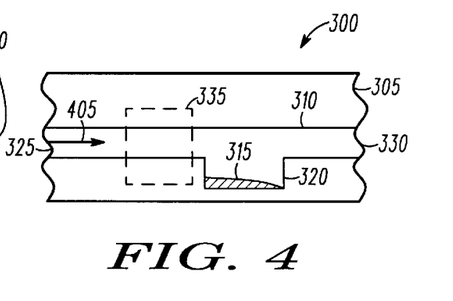

Referring to FIGS. 3 and 4, schematic representations of a close-open fluidic valve 300 are shown, in accordance with an embodiment of the present invention. The fluidic valve 300 has two mutually exclusive states, open and closed, and may have states of other description (for example, "initial", "in transition"). Not all the states are necessarily mutually exclusive. For example, the fluidic valve 300 is shown in FIG. 3 in an initial, closed state. The fluidic valve 300 comprises a portion of a fluid guiding structure 305, a fluid communication channel 310, a bi-phase valve element 315, a sink chamber 320, a heating zone 335, and a heat source (not shown in FIG. 3) thermally coupled to the heating zone 335. The fluid communication channel 310 fluidically couples an inlet port 325 to an outlet port 330, although in the state shown in FIG. 1 the fluid communication channel is blocked by the bi-phase valve element 315. An arrow 340 with an "X" over it indicates the presence of a controlled fluid that is under pressure at the inlet port 325. The portion of the fluid guiding structure 305 can be a portion of a larger fluid guiding structure, such as the one described with reference to FIGS. 1 and 2, and the inlet and outlet ports 325, 330 need not be at an outer surface of the overall fluid guiding structure. The bi-phase valve element 315 is implemented in a material that can be compound or mixture that has a state (typically defined either as a solid state or a highly viscous liquid state) at an operational temperature range having an upper limit in which it will normally clog the fluid communication channel in locations that are not the sink chamber 320 and another state that can be described as a liquid state or a state of low viscosity) at a switching temperature that is above the upper limit of the operational temperature range, in which state it can be moved by either gravity or fluid pressure, or both, to another location in the fluid communication channel 310, either in or out of the sink chamber 320. The operational temperature range and switching temperature of the bi-phase valve element are preferably compatible with the controlled fluid—that is, the controlled fluid's characteristics of interest are not undesirably affected by being at temperatures in the operational temperature range or the switching temperature, for the duration such temperatures are maintained during the operation of the fluidic valve 300. In accordance with the embodiments of the present invention described herein, the preferred material for the bi-phase valve element is a paraffin material that has a solid state below approximately 70 degrees Celsius and can be melted by heating above 70 degrees. When the paraffin is at approximately 80 degrees Celsius (which is 10 degrees above the upper limit of the high viscosity, or solid, state of the paraffin), the paraffin is in a low viscosity liquid state that allows it to be pushed within the fluidic guiding structure, while remaining as essentially one bulk of material. In an example of the close-open fluidic valve 300 implemented in accordance with this embodiment, the fluid guiding structure is made of plastic and the standard portions of the fluid communication channel 310 (i.e., those portions that are not the sink chamber 320) is a rectangular channel approximately 0.5 mm deep (e.g., into the plane of the paper in FIG. 3) and 1 mm wide (e.g., vertical in FIG. 3). When clogging the fluid communication channel 310, the paraffin bi-phase valve element 315 of this example blocks a controlled fluid that can exerts up to approximately 40 pounds per square inch (275,790.28 Pascal) of pressure without the blockage failing. The sink chamber 320 has dimensions large enough to ensure that when the melted bi-phase valve element passes therein, the additional volume in the sink chamber 320 can hold substantially all of the bulk of the bi-phase valve element 315 material, thereby leaving the sink chamber 320 with an opening of substantially the same cross sectional area as the non-expanded parts (standard portions) of the fluid communication channel 310. The heat source in this example is formed as a resistive heating element (in the manner of heaters 205, 210, 215 illustrated in FIG. 2) that, when activated, raises the temperature of the heating zone 335 of the fluid guiding structure 305 to which it is attached to about 90 degrees Celsius. The heating zone 335 is a region around the bi-phase valve element 315. The paraffin valve element 315 in this example, which melts at approximately 70 degrees Celsius, melts about 10 seconds after the heat source is activated and begins to flow toward the outlet port due to pressure exerted by the fluid at the inlet port, indicated in FIG. 3 by arrow 340.

Referring to FIG. 4, the valve element 315 is illustrated after the fluid pressure has moved it into the sink chamber 320 of the fluid communication channel, wherein gravity has moved it down into the sink chamber 320 where it has resolidified, leaving the fluid communication channel 310 and the close-open fluidic valve 300 in an open state, as indicated by the arrow 405 (without a cross on it).

Figure 5:
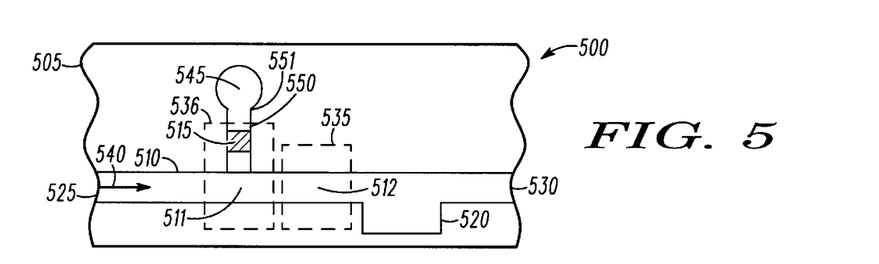
FIGS. 5, 6, and 7 are schematic drawings of an open-close-open fluidic valve 500, in accordance with an embodiment of the present invention.
Figure 6:
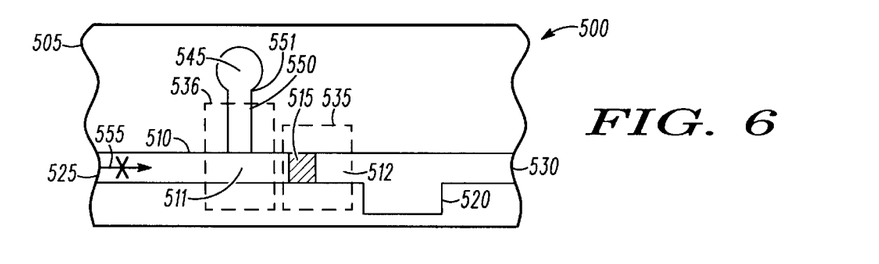
Figure 7:
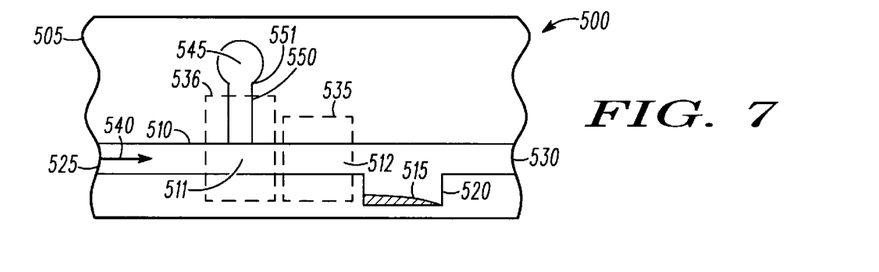

Referring to FIGS. 5, 6, and 7, schematic drawings of an open-close-open fluidic valve 500 are shown in accordance with an embodiment of the present invention. The fluidic valve 500 has two mutually exclusive states, open and closed, and may have states of other description (for example, "initial", "in transition"). Not all the states are necessarily mutually exclusive. The fluidic valve 500 is shown in FIG. 5 in an initial, open state. The fluidic valve 500 comprises a portion of a fluid guiding structure 505, a fluid communication channel 510, a bi-phase valve element 515, a sink chamber 520, two heating zones 535, 536, two heat source (not shown in FIG. 5) thermally coupled to the heating zones 535, 536, a valve element pump 545, a valve element source chamber 550, and a pump inlet port 551 of the valve element source chamber 550. The fluid communication channel 510 fluidically couples an inlet port 525 to an outlet port 530. The valve element source chamber 550 is coupled to the fluid communication channel 510 and has essentially the same cross sectional dimensions as the standard portions of the fluid communication channel 510. The valve element pump 545 is fluidically coupled to the valve element source chamber 550 at the pump inlet port 551. In the open state shown in FIG. 5, the bi-phase valve element 515 is in the valve element source chamber 550. An arrow 540 indicates the presence of a controlled fluid flowing under pressure from the inlet port 525 to the outlet port 530. The portion of the fluid guiding structure 505 can be a portion of a larger fluid guiding structure, and the inlet and outlet ports 525, 530 need not be at an outer surface of the overall fluid guiding structure. In the example shown in FIGS. 5–7, the materials and characteristics of the fluid guiding structure 505, the bi-phase valve element 515, the fluid communication channel 510 and the sink chamber 520 of the fluid communication channel 510 are the same as those of the respective items in FIGS. 3–4. When the temperature of the heating zone 536 is raised sufficiently to change the phase of the bi-phase valve element 515 to a melted phase, and the valve 15 element pump 545 is activated, the melted bi-phase valve element 515 is pushed into the fluid communication channel 510 by a fluid acted upon by the valve element pump 545, moving to a portion 511 of the fluid communication channel 510 that is within the heating zone 536. The melted bi-phase valve element 515 is then pushed, by a pressure exerted by the controlled fluid and the fluid acted upon by the valve element pump 545, into a portion 512 of the fluid communication channel 510 that is not heated at this time, and the bi-phase material resolidifies in the portion 512 of the fluid communication channel 510, as shown in FIG. 6, putting the fluidic valve 500 into a closed state, as indicated by the arrow 555 with an X on it. Then, the fluidic valve 500 can be switched to a open state in the manner described with reference to FIGS. 3–4 by activating the heat source that is thermally coupled to heating zone 535. It will be appreciated that, depending on the heat transfer characteristics of the fluid guiding structure 505 and the bi-phase valve element 515 and the flow rate of the melted bi-phase valve element 515, the heat sources coupled to heating zones 535 and 536 can be combined and controlled as one heat source to reduce the complexity of the fluidic valve 500.

Figures 8, 9:
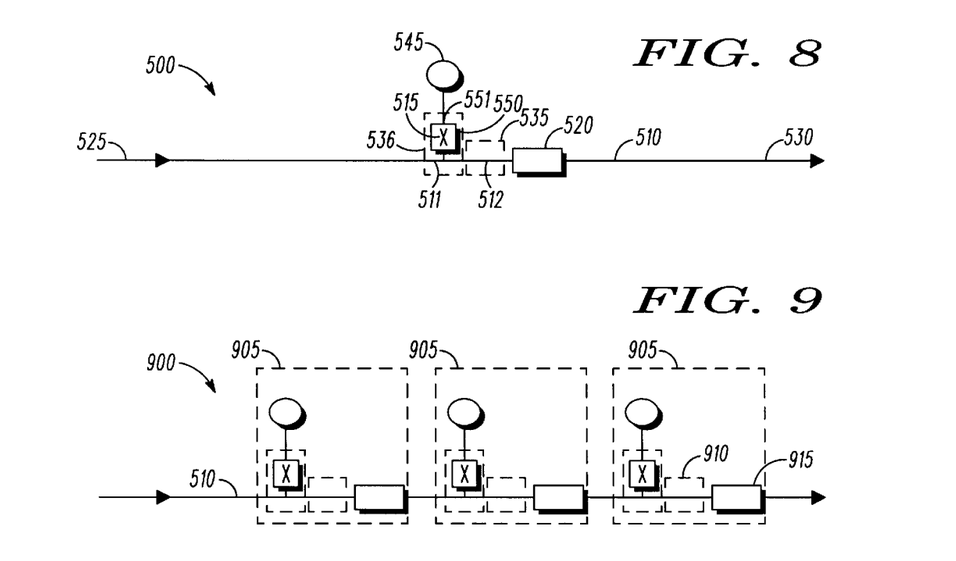
FIG. 8 is a simplified schematic of the open-close-open fluidic valve shown in FIG. 9, in accordance with the open-close-open embodiment of the present invention.
FIG. 9 is a simplified schematic of a toggle fluidic valve, in accordance with an embodiment of the present invention.

Referring to FIG. 8, a simplified schematic of the open-close-open fluidic valve 500 is shown, in accordance with the open-close-open embodiment of the present invention. FIG. 8 introduces simpler schematic symbols that are used without element numbers to describe other embodiments of the present invention in subsequent figures. The simpler schematic symbols in FIG. 8 have the same reference numbers as those in FIG. 7 and represent the same items described with reference to FIG. 7. The fluid guiding structure (e.g., 505) is left out of FIG. 8 and is also left out of the simplified schematics that follow FIG. 8, for simplicity. The valve element source chamber 550 is represented by a box in the simplified schematic of FIG. 8, but in FIG. 7 it is shown as a fluid channel that couples the fluid communication channel 510 to the valve element pump 545. In more detail, it is a portion of that fluid channel that contains the bi-phase valve element 515 during the initial state.

Referring to FIG. 9, a simplified schematic of a toggle fluidic valve 900 is shown, in accordance with an embodiment of the present invention. This embodiment is capable of providing an open-close-open-close-open-close operation, as is evident because it comprises three sections 905 that replicate elements (as shown) of the open-close valve described with reference to FIG. 7, which provide the open-close-open-close-open-close operation by activating the heating zones of the three sections 905 in sequence. It can also be used as fluidic valve that provides a truncated version of the open-close-open-close-open-close operation by simply not completing some of the operations. For example, by stopping the sequence before heating zone 910 is activated, which changes the operation of the toggle fluidic valve 900 to a open-close-open-close-open operation.

Figure 10:
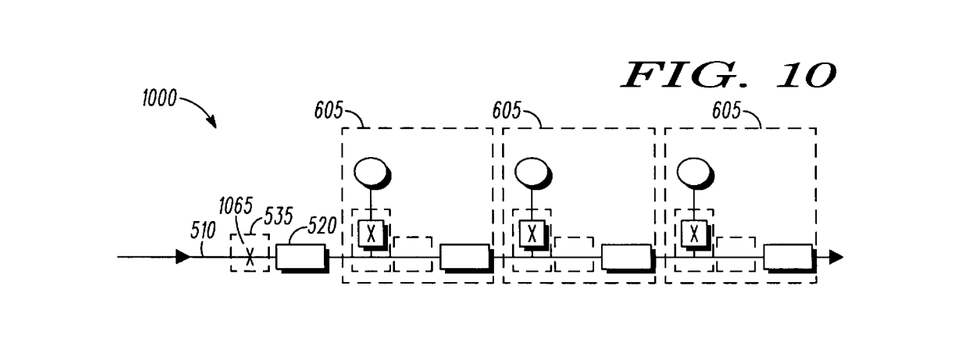
FIG. 10 is a simplified schematic of another toggle fluidic valve is shown, in accordance with an embodiment of the present invention.

Referring to FIG. 10, a simplified schematic of another toggle fluidic valve 1000 is shown, in accordance with an embodiment of the present invention. This differs from the toggle fluidic valve 900 by having an initial state that is closed. The initial state of the toggle fluidic valve 1000 is provided by a bi-phase valve element 1065 that is loaded into the fluid communication channel 510 when the toggle fluidic valve is fabricated. A corresponding heating zone 535 (coupled to a heat source) and a corresponding sink chamber 520 are also implemented, to allow a change of state from the initial closed state to an open state, in the manner described above. This bi-phase valve element 1065 and the bi-phase valve element 315 of FIG. 3 are alternatively called blocking bi-phase valve element in order to distinguish them from the bi-phase valve elements 515 that are loaded into the valve element source chambers 550.

Figure 11:
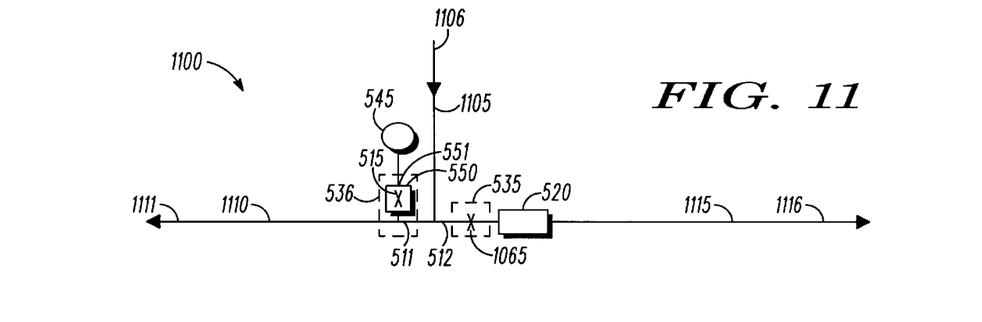
FIGS. 11–13 are simplified schematics of selecting fluidic valves, in accordance with an embodiment of the present invention.

Referring to FIG. 11, a simplified schematic of a selecting fluidic valve 1100 is shown, in accordance with an embodiment of the present invention. This selecting fluidic valve 1100 comprises a portion of a fluid guiding structure (not shown in FIG. 11), a fluid communication channel comprising a common branch 1105 that is fluidically coupled to a first branch 1110 and a second branch 1115, a bi-phase valve element 515 loaded at time of fabrication into a valve element source chamber 550 that is fluidically coupled to the first branch 1110 of the fluid communication channel, a valve element pump 545 coupled to the valve element source chamber 550, a heating zone 536 for the valve element source chamber 550, a blocking bi-phase valve element 1065, a heating zone 535 for the blocking bi-phase valve element 1065, a sink chamber 520, and two heat source (not shown in FIG. 11) thermally coupled to the heating zones 535, 536. The first branch 1110 fluidically couples a first switched fluid port 1111 to a common fluid port 1106. The second branch 1115 fluidically couples a second switched fluid port 1116 to the common fluid port 1106. In this example, common fluid port 1106 is an fluid inlet port for a controlled fluid and the first and second switched fluid ports 1111 and 1116 are outlets ports for the controlled fluid. FIG. 11 represents the selecting fluidic valve 1100 in a first state of at least two states that the selecting fluidic valve 1100 can assume, in which a controlled fluid can flow from the common fluid port 1106 out through the first switched fluid port 1111, but is blocked by the blocking bi-phase valve element 1065 from flowing out the second switched fluid port 1116. The blocking bi-phase valve element 1065 is placed in the second branch 1115 of the fluid communication channel, near an inlet end of the sink chamber 520 when the selecting fluidic valve 1100 is fabricated. When the heating zone 536 is heated, the bi-phase valve element 515 is melted and flows into the first branch 1110 of the fluid communication channel, where it blocks the flow of the controlled fluid out the first switched fluid port 1111. The bi-phase valve element is initially moved by pressure from the valve element pump 545 and gravity, and when it reaches the first branch 1110 of the fluid communication channel, it is moved by a combination of the pressure from the valve element pump 545 and pressure of the controlled fluid, until it resolidifies. When the heating zone 535 is heated, the blocking bi-phase valve element 1065 is melted and flows into the sink chamber 520 of the second branch 1115 of the fluid communication channel, thus opening the flow of the controlled fluid out the second switched fluid port 1116. The blocking bi-phase valve element 1065 is moved by pressure from the controlled fluid, and is moved to a downward area of the sink chamber 520 by gravity while it is melted. In accordance with a preferred version of this embodiment, the heating of zones 535 and 536 occurs essentially simultaneously, and the selectable fluidic valve 1100 is thereby switched to a second state in which the controlled fluid is directed to the second switched fluid port 1116.

Figure 12:
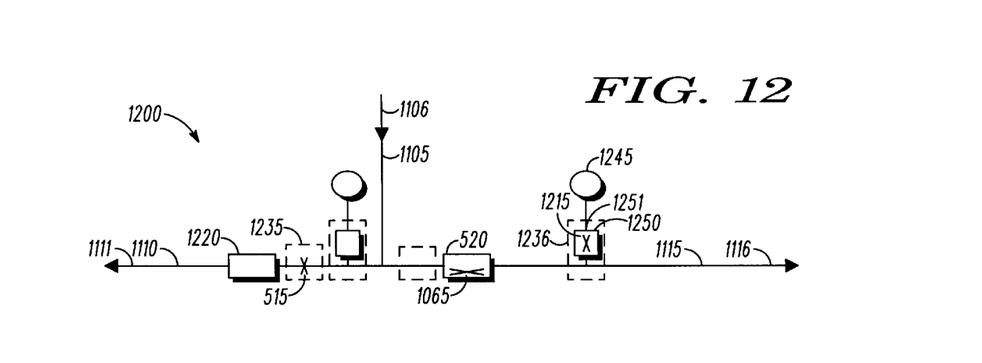

Referring to FIG. 12, a simplified schematic of a second selecting fluidic valve 1200, in accordance with an embodiment of the present invention. This selecting fluidic valve 1200 comprises the elements of the selecting fluidic valve 1100, and further comprises a bi-phase valve element 1215 loaded at time of fabrication into a valve element source chamber 1250 that is fluidically coupled to the second branch 1115 of the fluid communication channel, a valve element pump 1245 coupled to the valve element source chamber 1250, a heating zone 1235 for the valve element source chamber 1250, a heating zone 1236, a sink chamber 1220, and two heat sources (not shown in FIG. 12) thermally coupled to the heating zones 1235, 1236. FIG. 12 represents the selecting fluidic valve 1200 in a second state, which is the same as the second state achieved by the operation of the selecting fluidic valve 1100 described above. The bi-phase valve element 515 can now be moved into the sink chamber 1220 by activating the heating source coupled to the heating zone 1235, allowing the flow of the controlled fluid from the common fluid port 1106 to the first switched fluid port 1111, and the blocking bi-phase valve element 1065 can now be moved into the second branch 1115 of the fluid communication channel, blocking the flow of the controlled fluid to the second switched fluid port 1116. This puts the selecting fluidic valve 1200 back into a first state.

By now, it will be appreciated that the controlled fluid can be switched between the first and second switched fluid ports 1111 and 1116 (i.e., the first and second states) any finite number of times by adding to the selecting fluidic valve 1100 at least one set comprising a valve element chamber, a bi-phase valve element, and a valve sink chamber. For each set, the location of the coupling of the valve element source chamber to the fluid communication channel and the location of the sink chamber in each additional set are in different ones of the first and second branches of the fluid communication channel. Furthermore, the location of the coupling of the valve element source chamber to the fluid communication channel and the location of the additional sink chamber within each branch of the fluid communication channel are alternated along the branch. Other operations are also possible with these configurations, such as a state in which flow of the controlled fluid is closed to both switched fluid ports 1111,1116 or opened to both switched fluid ports 1111, 1116.

Figure 13:
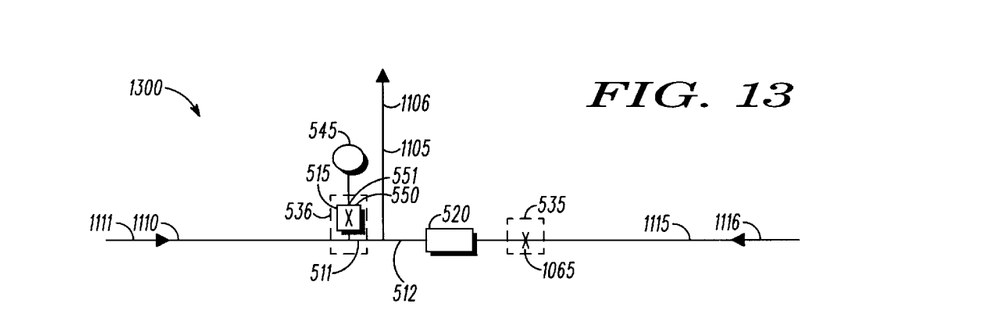

Referring to FIG. 13, a simplified schematic of a third selecting fluidic valve 1300 is shown, in accordance with an embodiment of the present invention. This selecting fluidic valve 1300 comprises a portion of a fluid guiding structure (not shown in FIG. 13), a fluid communication channel comprising a common branch 1105 that is fluidically coupled to a first branch 1110 and a second branch 1115, a bi-phase valve element 515 loaded at time of fabrication into a valve element source chamber 550 that is fluidically coupled to the first branch 1110 of the fluid communication channel, a valve element pump 545 coupled to the valve element source chamber 550, a heating zone 536 for the valve element source chamber 550, a blocking bi-phase valve element 1065, a heating zone 535 for the blocking valve element 1065, a sink chamber 520, and two heat source (not shown in FIG. 11) thermally coupled to the heating zones 535, 536. The first branch 1110 fluidically couples a first switched fluid port 1111 to a common fluid port 1106. The second branch 1115 fluidically couples a second switched fluid port 1116 to the common fluid port 1106. In this example, common fluid port 1106 is an fluid outlet port for one of a first and second controlled fluids, the first switched fluid port 1111 is a fluid inlet port for the first controlled fluid, and switched fluid port 1116 is a fluid inlet port for the second controlled fluid. FIG. 13 represents the selecting fluidic valve 1300 in a first state of at least two states that the selecting fluidic valve 1100 can assume, in which the first controlled fluid can flow from the first switched fluid port 1111 to the common fluid port 1106, while the second controlled fluid is blocked by the blocking bi-phase valve element 1065 from flowing from the second switched fluid port 1116 to the common fluid port 1106. The blocking valve element 1065 is placed in the second branch 1115 of the fluid communication channel, near an inlet end of the sink chamber 520 when the selecting fluidic valve 100 is fabricated. The initial location of the blocking bi-phase valve element 1065 and heating zone 535 in the selecting fluidic valve 1300 are spatially opposite the end of the sink chamber near which the blocking valve element 1065 and heating zone 535 are located in the initial state of selecting fluidic valve 1100. When the heating zone 536 is heated, the bi-phase valve element 515 is melted and flows into the first branch 1110 of the fluid communication channel, where it blocks the flow of the controlled fluid out the first fluid port 1111. The bi-phase valve element is initially moved by pressure from the valve element pump 545 and gravity, and when it reaches the first branch 1110 of the fluid communication channel, it is moved by a combination of the pressure from the valve element pump 545 and pressure of the controlled fluid, until it resolidifies. When the heating zone 535 is heated, the blocking bi-phase valve element 1065 is melted and flows into the sink chamber 520 of the second branch 1115 of the fluid communication channel, thus opening the flow of the second controlled fluid from the second switched fluid port 1116 to the common fluid port 1106. The blocking bi-phase valve element 1065 is moved by pressure from the second controlled fluid, and is moved to a downward area of the sink chamber 520 by gravity while it is melted. In accordance with a preferred version of this embodiment, the heating of zones 535 and 536 occurs essentially simultaneously, and the selectable fluidic valve 1100 is thereby switched to a second state in which the controlled fluid is selected from the second switched fluid port 1116.

It will be appreciated that the first and second states can repeated a finite number of times by adding one or more sets comprising a valve element chamber, a bi-phase valve element, and a valve sink chamber in a manner analogous to that described above with reference to FIG. 12.

Figure 14:
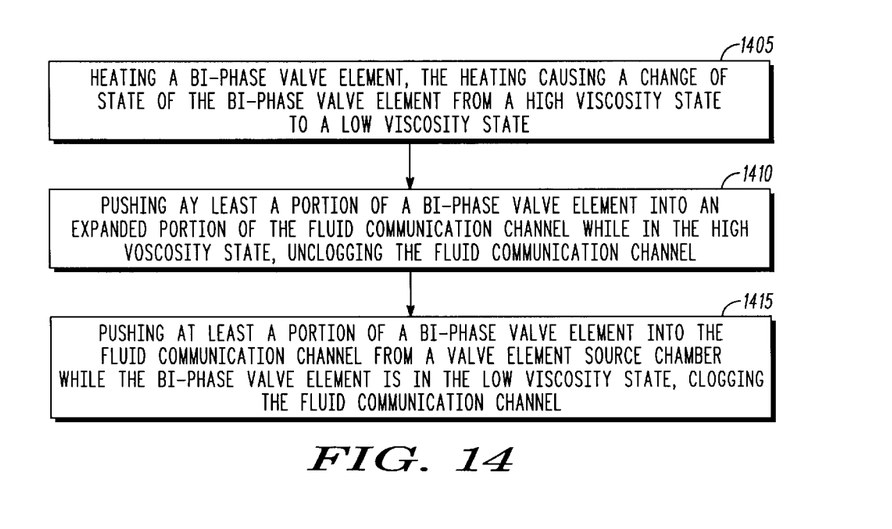
FIG. 14 is a flow chart of a method of switching a state of flow of a controlled fluid in a fluid communication channel, in accordance with an embodiment of the present invention. Skilled artisans will appreciate that elements in the figures are illustrated for simplicity and clarity and have not necessarily been drawn to scale. For example, the dimensions of some of the elements in the figures may be exaggerated relative to other elements to help to improve understanding of embodiments of the present invention.

Referring to FIG. 14, a flow chart of a method of switching a state of flow of a controlled fluid in a fluid communication channel is shown, in accordance with an embodiment of the present invention. The method allows combinations of a step 1405 of heating one or more bi-phase valve elements, a step 1410 of pushing at least a portion of one bi-phase valve element into an expanded portion of the fluid communication channel, and a step 1415 of pushing at least a portion of one bi-phase valve element into the fluid communication channel.

In the step 1405 of heating, a bi-phase valve element is heated and the heating causes a change of state of the bi-phase valve element from a high viscosity state to a low viscosity state.

In the step 1410 of pushing at least a portion of one of the bi-phase valve elements into an expanded portion of the fluid communication channel, at least a portion of a bi-phase valve element that clogs the fluid communications channel while in the high viscosity state is pushed, while in the low viscosity state, from a standard portion of the fluid communication channel to the expanded portion of the fluid communication channel. The pushing is caused by application of pressure to the fluid while the bi-phase valve element. The pressure is generated by gravitational force or a controlled fluid that is under pressure or a fluid that is pumped for the express purpose of moving the bi-phase valve element, or any combination of these forces. The portion pushed into the expanded portion of the communication channel is sufficient to unclog the fluid communication channel, permitting the flow of the controlled fluid through the portion of the communication channel that was clogged.

In the step 1415 of pushing at least a portion of a bi-phase valve element into the fluid communication channel, at least a portion of the bi-phase valve element is pushed from a valve element source chamber into the fluid communication channel using an application of pressure to the bi-phase valve element, while the bi-phase valve element is in the low viscosity state. The pressure is generated by a gravitational force or a controlled fluid under pressure or a fluid that is pumped for the express purpose of moving the bi-phase valve element, or any combination of these forces. The portion of the bi-phase valve element pushed into the fluid communication channel reverts to the high viscosity state and clogs the fluid communication channel, blocking-flow of the controlled fluid through the portion of the fluid communication channel that is clogged.

The expanded portion of the fluid communication channel has sufficient additional cross sectional area in comparison to a cross sectional area of a standard portion of the fluid communication channel to contain essentially the entirety of the bi-phase valve element.

It will be appreciated that the types of valves described herein can be designed for controlling organic fluids such as blood samples or DNA samples, using a wax bi-phase valve element that has a phase change temperatures that is compatible with the fluid and that does not undesirably become mixed with the controlled fluid. The description "a phase change temperatures that is compatible with the fluid" means that over the temperature range used to change and maintain the phase of the bi-phase valve element, the fluid being controlled by the fluidic valve remains in a liquid state and essential characteristics of the controlled fluid are not damaged. For example, if the fluid is a blood sample taken for testing of biological organisms, then the temperature range must be such that the biological organisms are not damaged." For different fluids that need to be controlled, the material for the bi-phase valve element can be one of a variety of paraffins (e. g., container, mould, dipping and microcrystalline, gel) and other waxes (e.g., soy wax, carnuba wax) having a variety of phase change temperatures and other properties of importance. There may exist inorganic bi-phase materials that are appropriate when used with other fluids and fluid guiding structures. For example, a low melting temperature metal alloy may be appropriate for a one time emergency valve in a engine control that controls the power steering fluid. Among the variety of possible bi-phase valve element materials, some may be used at temperatures at which the material is not clearly ever in a solid, but is in a high viscosity state at a low operational temperature such that it can effectively clog the fluid communication channel at parts that are not the expanded portion, and at a high operational temperature is in a low viscosity state that allows it to be moved by the pressure of the controlled fluid and/or gravity.

It will be further appreciated that although the heat sources have been described above as being resistive patterns, the heat source could be of any other type. Two examples are peltier heaters and chemical heaters. Chemical heaters could be implemented as two chemicals in two chambers that become connected using a fluidic valve of the type described herein. Thus, a small peltier heater could activate a large area chemical heater, or a chemical heater could activate another chemical heater in a delayed fashion.

It will be further appreciated that the shape and orientation of the expanded portions (e.g., 320, 520) of the fluid communication channels (e.g., 310, 510) are not constrained to that implied by the illustrations in FIGS. 3–8. For example, a sink chamber could have a circular cross section and the standard portions of the fluid communication channel could couple to the sink chamber at the axis of the sink chamber cross section. Also, the transition between the sink chamber and the other parts of the fluid communication channel could be gradual instead of abrupt (as represented in FIGS. 3–5). Such configuration differences of the sink chamber (circular cross section, gradual transition) could be appropriate in situations where gravity is not relied upon to guide the melted (low viscosity) phase of the bi-phase material while it is changing to the resolidified (high viscosity) phase. It may also be appropriate for the sink chamber to be at a bend of a fluid communication channel.

While gravity has been described above as a force that is involved in moving the controlled fluids in desired directions, it will be appreciated that with an appropriate combination of small communication channels and correspondingly small co-axial sink chambers, along with a bi-phase valve element material chosen for appropriate capillary characteristics, the bi-phase valve element material may be moved contrary to the direction of the gravitational force and may be moved away from a central flow portion of the sink chambers. It will be further appreciated that in some instances, such as moving a bi-phase valve element from a valve element source chamber into a communication channel, the pressure of the controlled fluid may not be needed to accomplish the desired relocation of the bi-phase valve element. In the foregoing specification, the invention has been described with reference to specific embodiments. However, one of ordinary skill in the art appreciates that various modifications and changes can be made without departing from the scope of the present invention as set forth in the claims below. Accordingly, the specification and figures are to be regarded in an illustrative rather than a restrictive sense, and all such modifications are intended to be included within the scope of present invention.

It will be appreciated that a fluidic valve implemented in accordance with the embodiments of the present invention can be beneficially used in a fully integrated biomicrofluidic device, for example, one that can both amplify and electronically detect high abundance DNA targets (e.g., human genomic DNA from diluted blood solution or other bodily fluids) and perform SNP detection assays, as well as many other types of fluidic systems. By appropriate arrangement of the elements of the present invention, a low cost single use or multiple use valve arrangement can be implemented.

Benefits, other advantages, and solutions to problems have been described above with regard to specific embodiments. However, the benefits, advantages, solutions to problems, and any element(s) that may cause any benefit, advantage, or solution to occur or become more pronounced are not to be construed as a critical, required, or essential features or elements of any or all the claims. As used herein, the terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus.

What is claimed is:

1. A method for switching a state of flow of a fluid in a fluid communication channel, comprising:

heating a bi-phase valve element that clogs the fluid communication channel, the heating causing a change of state of the bi-phase valve element from a high viscosity state to a low viscosity state; and pushing at least a portion of the bi-phase valve element into a sink chamber of the fluid communication channel by application of pressure to the fluid while the bi-phase valve element is in the low viscosity state, wherein the portion pushed into the sink chamber is sufficient to unclog the fluid communication channel.

2. The method according to claim 1, wherein the pressure is generated by at least one of a gravitational force and the fluid and a pumped fluid.

3. A method for switching a state of flow of a fluid in a fluid communication channel, comprising:

heating a bi-phase valve element that is in a valve element source chamber fluidically coupled to the fluid communication channel, the heating causing a change of state of the bi-phase valve element from a high viscosity state to a low viscosity state; and pushing at least a portion of the bi-phase valve element from the valve element source chamber into the fluid communication channel using a pumped fluid while the bi-phase valve element is in the low viscosity state, wherein the portion pushed into the fluid communication channel reverts to the high viscosity state and clogs the fluid communication channel.

4. A method for switching a state of flow of a fluid in a fluid communication channel of a fluid guiding structure, comprising at least one of two sets {(a) and (b)} and {(c) and (d)}:

(a) heating a bi-phase valve element that clogs the fluid communication channel, the heating causing a change a state of the bi-phase valve element from a high viscosity state to a low viscosity state;

(b) pushing at least a portion of the bi-phase valve element into a sink chamber of the fluid communication channel by an application of pressure to the fluid while the bi-phase valve element is in the low viscosity state, wherein the portion pushed into the sink chamber is sufficient to unclog the fluid communication channel;

(c) heating a bi-phase valve element that is in a valve element source chamber fluidically coupled to the fluid communication channel, the heating causing a change a state of the bi-phase valve element from a high viscosity state to a low viscosity state; and (d) pushing at least a portion of the bi-phase valve element from the valve element source chamber into the fluid communication channel by using a pumped fluid while the bi-phase valve element is in the low viscosity state, wherein the portion pushed into the fluid communication channel solidifies and clogs the fluid communication channel.

5. The method according to claim 4, wherein the bi-phase valve element comprises a material that is in a high viscosity state over an operational temperature range having an upper limit and is in a low viscosity state at an activation temperature that is at least 10 degrees Celsius above the upper limit.

6. The method according to claim 4, wherein the bi-phase valve element comprises a material that is in a low viscosity state above 80 degrees Centigrade.

7. The method according to claim 4, wherein the bi-phase valve element comprises a paraffin material that melts at approximately 70 degrees Celsius.

8. The method according to claim 4, wherein the sink chamber of the fluid communication channel has sufficient additional cross sectional area in comparison to a cross sectional area of a standard portion of the fluid communication channel to contain essentially an entirety of a bi-phase valve element.

9. A fluidic valve for switching a state of flow of a controlled fluid, comprising:
   a fluid guiding structure
   a fluid communication channel having at least one fluid inlet port and one fluid outlet port; and
   at least one of
      a bi-phase valve element source chamber having a pump inlet, fluidically coupled to the fluid communication channel and
      a bi-phase element sink chamber that is an expanded portion of the fluid communication channel.

10. The fluidic valve according to claim 9, further comprising at least one bi-phase valve element, wherein the at least one bi-phase valve element comprises a material that is in a high viscosity state over an-operational temperature range of the fluidic valve having an upper limit and is in a low viscosity state at an activation temperature that is at least 10 degrees Celsius above the upper limit.

11. The fluidic valve according to claim 9, further comprising at least one bi-phase valve element, wherein the at least one bi-phase valve element comprises a material that is in a low viscosity state above 80 degrees Centigrade.

12. The fluidic valve according to claim 9, further comprising at least one bi-phase valve element, wherein the at least one bi-phase valve element comprises a paraffin material that melts at approximately 70 degrees Celsius.

13. The fluidic valve according to claim 9, wherein the bi-phase element sink chamber of the fluid communication channel has sufficient additional cross sectional area in comparison to a cross sectional area of a standard portion of the fluid communication channel to contain essentially an entirety of a bi-phase valve element.

14. A fluidic system comprising the fluidic valve according to claim 9.

15. A micro-biofluidic device comprising the fluidic valve according to claim 9.

16. A fluidic valve having a state that can be one of opened or closed, comprising:
   a fluid guiding structure;
   a fluid communication channel, formed within the fluid guiding structure, and fluidically coupling a fluid inlet port and a fluid outlet port;
   a valve element source chamber, formed within the fluid guiding structure, fluidically coupled to the fluid communication channel and having a-pump inlet port;
   a bi-phase valve element that is in the valve element source chamber while the fluidic valve is in an initial state that is the opened state; and
   a heat source that can change the state of the fluidic valve by heating the bi-phase valve element.

17. The fluidic valve according to claim 16, wherein a portion of the bi-phase valve element sufficient to block the fluid communication channel is in the fluid communication channel during the closed state.

18. A fluidic valve having a state that can be one of opened or closed, comprising:
   a fluid guiding structure;
   a fluid communication channel, formed within the fluid guiding structure, fluidically coupling a fluid inlet port to a fluid outlet port;
   a sink chamber, formed within the fluid guiding structure as an expanded portion of the fluid communication channel;
   a bi-phase valve element that is in the fluid communication channel between the fluid inlet port and the sink chamber while the fluidic valve is in an initial state that is closed; and
   a heat source that can change the state by heating the bi-phase valve element.

19. The fluidic valve according to claim 18, wherein a portion of the bi-phase valve element sufficient to open the fluid communication channel is in the sink chamber during the opened state.

20. A fluidic valve having a state that can be one of opened or closed, comprising:
   a fluid guiding structure;
   a fluid communication channel, formed within the fluid guiding structure, fluidically coupling a fluid inlet port to a fluid outlet port;
   a valve element source chamber, formed within the fluid guiding structure, fluidically coupled to the fluid communication channel and having a pump inlet port;
   a sink chamber, formed within the fluid guiding structure as an expanded portion of the fluid communication channel;
   a bi-phase valve element that is in the valve element source chamber while the fluidic valve is in an initial state; and
   at least one heat source that can change the state of the fluidic valve by heating the bi-phase valve element.

21. The fluidic valve according to claim 20, wherein the bi-phase valve element is in the fluid communication channel between the fluid inlet port and the sink chamber while the fluidic valve is in a closed state.

22. The fluidic valve according to claim 20, wherein the initial state is the opened state, and wherein the valve element source chamber is coupled to the fluid communication channel on an inlet side of the sink chamber.

23. The fluidic valve according to claim 20, further comprising a blocking bi-phase valve element, wherein the initial state is the closed state, and wherein the blocking bi-phase valve element can be heated by at least one of the at least one heat source to change the state.

24. The fluidic valve according to claim 23, wherein the bi-phase valve element is in the valve element source chamber and the blocking bi-phase valve element is in the fluid communication channel at a location on an inlet side of the valve sink chamber during the initial state.

25. The fluidic valve according to claim 20, comprising one or more additional valve element chambers having corresponding additional bi-phase valve elements therein and one or more corresponding additional sink chambers, wherein locations of couplings of the additional valve element source chambers to the fluid communication channel and locations of the additional sink chambers are alternated along the fluid communication channel.

26. The fluidic valve according to claim 25, wherein the additional bi-phase valve element corresponding to each additional valve element source chamber is in the valve element source chamber during the initial state.

27. The fluidic valve according to claim 25, further comprising a blocking bi-phase valve element in the fluid communication channel during the initial state, which is the closed state.

28. A fluidic valve that has a state that can be one of a first state and a second state, comprising:

a fluid guiding structure;

a fluid communication channel, formed within the fluid guiding structure, having a first branch that fluidically couples a fluid inlet port to a first fluid outlet port, and a second branch that fluidically couples the fluid inlet port to a second fluid outlet port;

a valve element source chamber, formed within the fluid guiding structure, fluidically coupled to the first branch of the fluid communication channel and having a pump inlet port;

a sink chamber, formed within the fluid guiding structure as an expanded portion of the second branch of the fluid communication channel;

a bi-phase valve element that is in the valve element source chamber during the first state in which fluid can only flow from the fluid inlet port to the first fluid outlet port;

a blocking bi-phase valve element is in the second branch of the fluid communication channel, between the sink chamber of the second branch and a junction of the first and second branches, during the first state; and at least one heat source that can change the state of the fluidic valve by heating one or both of the bi-phase valve element and the blocking bi-phase valve element.

29. The fluidic valve according to claim 28, wherein the bi-phase valve element is in the fluid communication channel and the blocking bi-phase valve element is in the sink chamber of the second branch during the second state, in which fluid can only flow from the fluid inlet port to the second fluid outlet port.

30. A fluidic valve having a state that can be one of a first or second state, comprising:

a fluid guiding structure;

a fluid communication channel, formed within the fluid guiding structure, having a first branch that fluidically couples a first switched fluid port to a common fluid port, and a second branch that fluidically couples a second switched fluid port to the common fluid port;

a valve element source chamber, formed within the fluid guiding structure, fluidically coupled to the first branch of the fluid communication channel and having a pump inlet port;

a sink chamber, formed within the fluid guiding structure as an expanded portion of the second branch of the fluid communication channel;

a bi-phase valve element;

a blocking bi-phase valve element; and at least one heat source that can change the state of the fluidic valve by heating one or both of the bi-phase valve element and blocking bi-phase valve element.

31. The fluidic valve according to claim 30, wherein the bi-phase valve element is in the valve element source chamber and the blocking bi-phase valve element is in the second branch of the fluid communication channel near an inlet end of the sink chamber during an initial state in which fluid can flow only between the first switched fluid port and the common fluid port of the fluid communication channel.

32. The fluidic valve according to claim 30, further comprising at least one set comprising an valve element chamber, a bi-phase valve element, and a valve sink chamber, wherein a location of the coupling of the valve element source chamber to the fluid communication channel and a location of the sink chamber in each additional set are in different ones of the first and second branches of the fluid communication channel.

\* \* \* \* \*